US006826254B2

United States Patent
Mihara et al.

(10) Patent No.: US 6,826,254 B2
(45) Date of Patent: Nov. 30, 2004

(54) RADIATION APPLYING APPARATUS

(75) Inventors: Kazumasa Mihara, Hiroshima-ken (JP); Yuichiro Kaminou, Aichi-ken (JP); Akira Ishibashi, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/285,441

(22) Filed: Nov. 1, 2002

(65) Prior Publication Data
US 2003/0048875 A1 Mar. 13, 2003

Related U.S. Application Data

(63) Continuation of application No. PCT/JP02/01836, filed on Feb. 28, 2002.

(30) Foreign Application Priority Data

Mar. 2, 2001 (JP) .......................................... 2001-058732

(51) Int. Cl.$^7$ ............................. G21K 5/00; H01J 33/00
(52) U.S. Cl. ............................ 378/64; 378/65; 378/119; 378/197; 250/492.3; 250/493.1; 315/111.81; 315/505
(58) Field of Search .............................. 378/64, 65, 119, 378/196, 197, 198; 250/492.1, 492.3, 493.1, 505.1; 315/111.81, 505

(56) References Cited

U.S. PATENT DOCUMENTS

| | | | | |
|---|---|---|---|---|
| 4,020,431 A | * | 4/1977 | Saunders | 333/256 |
| 4,628,523 A | | 12/1986 | Heflin | |
| 4,726,046 A | * | 2/1988 | Nunan | 378/65 |
| 4,979,202 A | * | 12/1990 | Siczek et al. | 378/198 |
| 5,635,721 A | * | 6/1997 | Bardi et al. | 250/492.3 |
| 5,933,335 A | * | 8/1999 | Hitchcock et al. | 363/25 |
| 5,963,615 A | * | 10/1999 | Egley et al. | 378/65 |
| 6,052,435 A | * | 4/2000 | Hernandez-Guerra et al. | 378/150 |
| 6,094,760 A | | 8/2000 | Nonaka et al. | |
| 6,327,339 B1 | * | 12/2001 | Chung et al. | 378/121 |
| 6,529,387 B2 | * | 3/2003 | Kirbie | 363/16 |

FOREIGN PATENT DOCUMENTS

| | | |
|---|---|---|
| JP | 57-185872 | 11/1982 |
| JP | 3-15448 | 1/1991 |
| JP | 7-51395 | 2/1995 |
| JP | 2001-9050 | 1/2001 |
| WO | WO 91/16948 | 11/1991 |

\* cited by examiner

*Primary Examiner*—Allen C. Ho
(74) *Attorney, Agent, or Firm*—Armstrong, Kratz, Quintos, Hanson & Brooks, LLP

(57) ABSTRACT

An x-ray treatment apparatus includes an x-ray generating device, a head unit, a manipulator and a microwave source. The x-ray generating device produces x-rays, by letting electrons, which have been emitted from an electron gun, be accelerated by a linear accelerator and strike a target. The acceleration of electrons is effected by microwaves. The x-ray generating device is accommodated in the head unit. The head unit is attached to a distal end portion of the manipulator. The manipulator positions the head unit such that x-rays emitted from the head unit may be applied to a part for medical treatment in a patient. The microwave source is disposed at a proximal end portion of the manipulator. Microwaves are propagated from the microwave source to the accelerator through a waveguide.

9 Claims, 2 Drawing Sheets

RADIATION APPLYING APPARATUS

CROSS-REFERENCE TO RELATED APPLICATIONS

This is a Continuation Application of PCT Application No. PCT/JP02/01836, filed Feb. 28, 2002, which was not published under PCT Article 21(2) in English.

This application is based upon and claims the benefit of priority from the prior Japanese Patent Application No. 2001-058732, filed Mar. 2, 2001, the entire contents of which are incorporated herein by reference.

BACKGROUND OF THE INVENTION

1. Field of the Invention

A radiation applying apparatus according to the present invention is used, for example, for treatment in medical fields, wherein radiation is applied from the outside to a focus within a human body.

2. Description of the Related Art

There is a radiation applying apparatus for use in medical or industrial fields. The radiation applying apparatus is used for tests and treatment of patients in medical fields, or for non-destructive testing in industrial fields.

In the field of medical treatment, there is radiation treatment to treat a focus at a deep region in the human body, applying the radiation, e.g. x-rays, from the outside to pass through the focus, and killing the cells of the focus. FIG. 3 shows an x-ray treatment apparatus 51 as an example of the radiation applying apparatus to be used for the radiation treatment. The x-ray treatment apparatus 51 has a platform 52, an articulated robot arm 53 and a head unit 54. The platform 52 is fixed on the floor. The robot arm 53 couples the platform 52 and head unit 54. The head unit 54 has an x-ray emitting port 55 at a distal end thereof. The x-ray treatment apparatus 51 is controlled by a control unit (not shown) so as to direct the x-ray emitting port 55 toward a focus in the patient.

X-rays to be emitted from the x-ray emitting port 55 are produced by causing electrons from an electron gun to strike on a target of tungsten, etc. The radiation treatment requires more intense x-rays than x-rays used in x-ray transmission photography. The radiation treatment apparatus hits the target by accelerated electrons using a linear accelerator that accelerates electrons with microwaves in order to produce the high-intensity x-rays.

For example, a magnetron and a Klystron are known as microwave emission sources. Compared to the Klystron, the magnetron can easily be reduced in size. Thus, the magnetron is advantageously used as a microwave source provided in the head unit 54 of x-ray treatment apparatus 51.

The electron gun, target and linear accelerator, which are necessary for producing x-rays, are carried in the head unit 54 along with a microwave source for operating the linear accelerator and a transformer for activating the microwave source. Power cables and control cables necessary for these elements and a water-cooling pipe for the target are provided through the robot arm 53.

In the x-ray treatment apparatus 51, the main part is accommodated in the head unit 54, and the head unit 54 is moved by the robot arm 53. This structure is advantageous in that the head unit 54 and robot arm 53 can be independently developed.

As regards the x-ray treatment apparatus 51, however, since the equipment for generating x-rays is mounted in the head unit 54, the head unit 54 attached at the distal end of the robot arm 53 is huge and heavy. Consequently, when the patient is treated, the range of motion of the x-ray treatment apparatus 51 is limited. The robot arm 53, which supports the head unit 54, becomes necessarily strong and large. Hence, the operation of the robot arm becomes slow, and exact positioning thereof becomes difficult.

A microwave output of the magnetron is small. If a small-sized magnetron is adopted for mounting in the head unit 54, the x-ray treatment apparatus 51 is unable to obtain a large microwave output. In this case, since the x-ray treatment apparatus 51 cannot produce high-intensity x-rays, the treatment effect on a focus located deep in the human body is limited.

Besides, since the magnetron produces microwaves by self-excited oscillation, the output of the magnetron is unstable. Consequently, the x-ray output is also unstable. Furthermore, the life of the magnetron is shorter than that of the Klystron, and frequent maintenance of the head unit 54 is required. Compared to the Klystron, the reliability of the magnetron as apparatus is low.

Under the circumstances, attention has been paid to the use of a Klystron as a microwave source, which ensures a stable output and a long life. However, the Klystron has a larger size than the magnetron and is less suitable for a microwave source to be mounted in the head unit 54.

BRIEF SUMMARY OF THE INVENTION

The present invention aims at providing a radiation applying apparatus capable of applying a high radiation output, with a small-sized, light-weight head unit which emits radiation.

A radiation applying apparatus according to an embodiment of the invention has a positioning device for positioning a head unit with a multi-axis control. Devices associated directly with generation of radiation are mounted in the head unit. Other devices are disposed at a proximal end portion of the radiation applying apparatus. The head unit can be reduced in size and weight, and the device for positioning the head unit can be reduced in weight.

In a case where radiation is x-rays, an electron gun, a target and an accelerator are mounted in the head unit as the devices associated directly with generation of x-rays. The electron gun emits electrons. The target emits x-rays upon being hit by the electrons. The accelerator accelerates the electrons emitted from the electron gun toward the target. A power source which supplies the accelerator with power is placed apart from the head unit. The acceleration of electrons is effected by microwaves. Microwaves are supplied from a microwave source provided as the power source. A positioning device is a cantilever-type manipulator. A waveguide for propagating the microwaves is provided along the manipulator from the microwave source to the head unit. The radiation applying apparatus employs a Klystron as the microwave source. The Klystron has a long life and can supply a stable radiation output. The microwave source provided as the power source is disposed at the proximal end portion of the radiation applying apparatus, whereby the head unit is reduced in size and weight. Therefore, a load on the manipulator can be decreased, and the manipulator reduced in weight.

In this radiation applying apparatus, the positioning device is provided movable along rails. Thereby, the number of movable connection portions (joints) necessary for positioning the head unit and the number of flexible portions of the waveguide can be reduced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
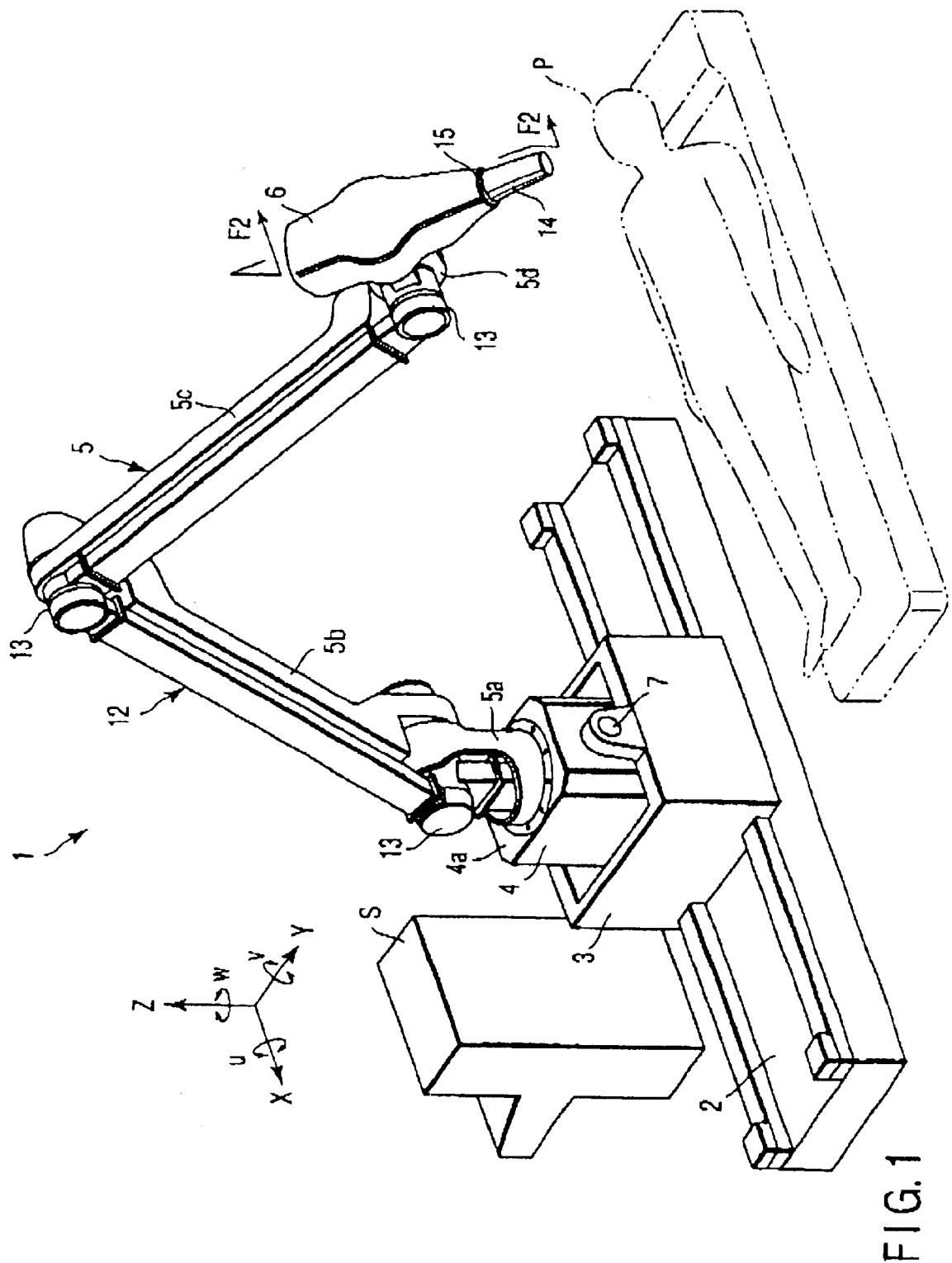
FIG. 1 is a perspective view showing an x-ray treatment apparatus which is a radiation applying apparatus according to an embodiment of the present invention.

A radiation applying apparatus according to an embodiment of the present invention will now be described by referring to an x-ray treatment apparatus 1 shown in FIG. 1 by way of example. For easier understanding of the operation, 3-axis (X-Y-Z) orthogonal coordinates and rotational directions u, v and w on the respective axes are applied.

The x-ray treatment apparatus 1 comprises rails 2; a platform, e.g. a carrier 3; a microwave source 4; a manipulator 5; and a head unit 6. The rails 2 are laid in the X-axis direction. The carrier 3 is set on the rails so as to be movable in the X-axis direction. The carrier 3 carries a main power supply of the x-ray treatment apparatus 1, a high-voltage power supply for supplying power to microwave source 4, manipulator 5 and head unit 6. The carrier 3 is equipped with a drive unit, etc., by which the carrier 3 runs on the rails. The microwave source 4 is rotatively supported by trunnions 7 attached on both sides thereof. The microwave source 4 is rotated in the direction v by a servomotor (not shown) provided between itself and the carrier 3. The microwave source 4 is connected to the high-voltage power supply mounted on the carrier 3 and produces microwaves. A magnetron or a Klystron is used as the microwave source 4. It is preferable to adopt the Klystron, which has a longer life and produces a more stable output than the magnetron. The manipulator 5 is attached to a top portion 4a of the microwave source 4 so as to be rotatable in the direction w. The manipulator 5 has a base portion 5a, a first arm 5b, a second arm 5c and a head mount 5d, which are coupled to be rotatable in the direction u. The head unit 6 is coupled to the head mount 5d so as to be rotatable relative to the head mount 5d. Each of the coupled elements incorporates a servomotor (not shown) that is controlled by a control unit S. Thus, the manipulator 5 is able to direct the head unit 6 toward a focus of a patient P.

Figure 2:
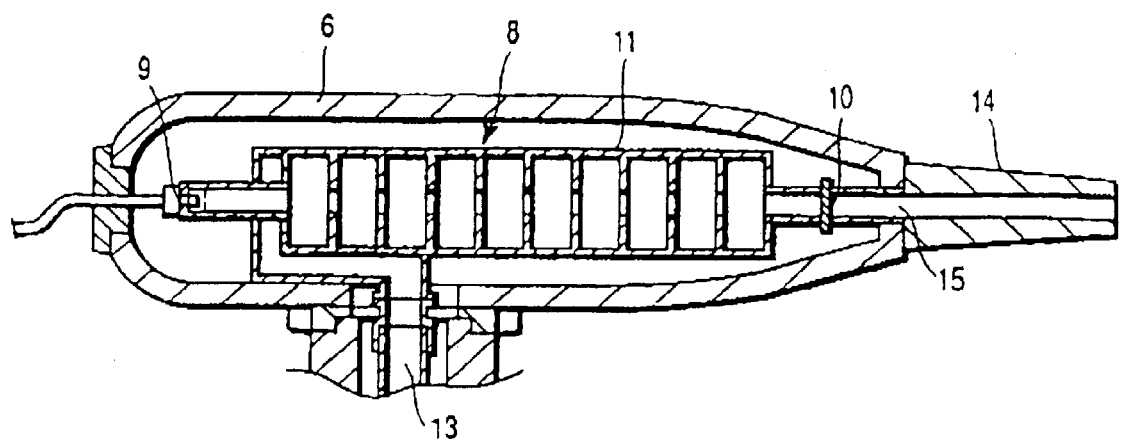
FIG. 2 is a cross-sectional view of a head unit, taken along line F2—F2 in FIG. 1.
Figure 3:
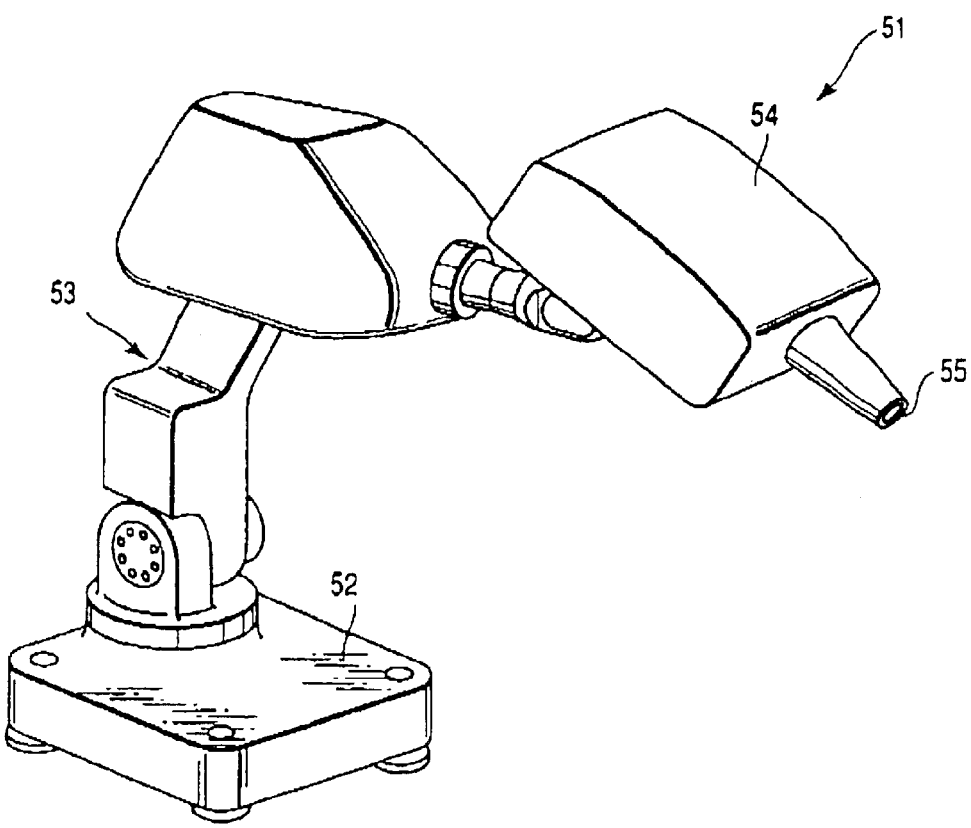
FIG. 3 is a perspective view showing a conventional x-ray treatment apparatus.

As is shown in FIG. 2, the head unit 6 accommodates, for example, an x-ray generator 8 as a radiation generating device. The x-ray generator 8 comprises an electron gun 9, a target 10, and a linear accelerator 11 provided as an accelerator. The electron gun 9 emits electrons toward a target 10. When electrons have struck the target 10, the target 10 radiates x-rays from the opposite surface. The linear accelerator 11 is arranged between the electron gun 9 and target 10 and accelerates the electrons emitted from the electron gun 9 toward the target 10 with microwaves. The x-rays emitted from the target 10 come out through an x-ray emitting port 15 formed at an end portion of the head unit 6. A collimator 14 for collimating the x-rays emitted from the x-ray radiation port 15 is attached to the end portion of the head unit 6.

The microwaves used in the linear accelerator 11 are supplied by the microwave source 4 set at a proximal end portion of the manipulator 5. The oscillated microwaves propagate through a waveguide 12 up to the linear accelerator 11 of head unit 6. The waveguide 12 is arranged along the manipulator 5 from the microwave source 4 to the head unit 6 as shown in FIG. 1. The waveguide 12 is provided with rotary RF (Radio Frequency) couplers 13 at positions corresponding to connection points between the top portion 4a of microwave source 4 and the base portion 5a of the manipulator, between the base portion 5a and first arm 5b, between the first arm 5b and second arm 5c, between the second arm 5c and head mount 5d, and between the head mount 5d and head unit 6, respectively. The waveguide 12 is flexible along with the manipulator 5.

In this x-ray treatment apparatus 1, the control unit S is disposed apart from the carrier. When a treatment position of the patient P is inputted to the control unit S, the control unit S controls the servomotors of the manipulator 5 and carrier 3 and the drive unit of the carrier 3 so that x-rays may be applied to the treatment part. Thus, the x-ray emitting port 15 of the head section 6 is directed to the treatment part. Once the head unit 6 is positioned, the control unit S activates the microwave source 4 and electron gun 9. Electrons emitted from the electron gun 9 are accelerated by microwaves while the electrons are traveling through the linear accelerator 11. The accelerated electrons strike the target 10. When the accelerated electrons have struck one side of the target 10, the target 10 emits x-rays from the other side. The radiating angle of the x-rays is narrowed by the collimator 14. The resultant x-rays are applied to the treatment part of the patient P.

When a predetermined dose of x-ray has been applied from the determined x-ray irradiation position, the head unit 6 of the x-ray treatment apparatus 1 is moved to the next x-ray irradiation position. In this x-ray treatment apparatus 1, in order to apply x-rays to the treatment part in multiple directions, the head unit 6 is moved around the treatment part inputted by the control unit S. The x-ray treatment apparatus 1 repeatedly applies the x-rays while altering the position and angle of the head unit 6, so that the radiated x-rays may pass through the treatment part.

As has been described above, the x-ray treatment apparatus 1 according to the embodiment, is equipped with the electron gun 9, target 10 and acceleration tube 11 in the head unit 6, and the microwave source 4, transformer, power supply unit, etc. are disposed at the base portion 5a of the manipulator 5. In short, in this x-ray treatment apparatus 1, the equipment directly related to the x-ray generation is amounted in the head unit 6, and the other equipment is disposed at the base portion 5a of manipulator 5. Thus, the head unit 6 is reduced in size and weight. According to the x-ray treatment apparatus 1, since the head unit 6 is small, the movement range of the head unit 6 is less restricted when the focus in the patient P is treated. In addition, mental stress on the patient P, which occurs when a large apparatus moves nearby, is reduced. In this x-ray treatment apparatus 1, since the head unit 6 is reduced in weight, the manipulator that supports the head unit 6 can also be reduced in weight and simplified. Therefore, the operation of the x-ray treatment apparatus 1 can be controlled more quickly and exactly. Instead of reducing the head unit 6 in size and weight, a linear accelerator with a higher output may be provided to produce a higher x-ray output.

In this x-ray treatment apparatus 1, since the microwave source 4 is disposed apart from the head unit 6 on the side of the base portion 5a of manipulator 5, the microwave source 4 with a high output can be provided without restricting the movement range of the head unit 6 and the operation of manipulator 5. In the x-ray treatment apparatus 1, since the Klystron is adopted as the microwave source 4, a stable microwave output can be obtained. The x-ray treatment apparatus 1 is highly reliable as a radiation applying apparatus, since an x-ray output, which is produced when the electrons accelerated by microwaves have struck the target 10, is also stable. Since the Klystron has a longer life than the magnetron, the operation efficiency of the radiation applying apparatus is enhanced.

In the x-ray treatment apparatus 1, the carrier 3 is movable along the rails 2 in the direction X, and the trunnions 7 permit the microwave source 4 to rotate in the direction v. In the x-ray treatment apparatus 1, the elements other than the manipulator 5 have the degree of freedom. Thus, the degree of freedom (the number of rotational axes) required for the manipulator 5 in positioning the head unit 6 can be reduced. Since the number of connection points (joints) of the manipulator 5 of this x-ray treatment apparatus 1 can be reduced, the number of rotary RF couplers 13 provided at the bending portions of the waveguide 12 arranged along the manipulator 5 can be reduced. Therefore, the manipulator 5 of x-ray treatment apparatus 1 is simplified.

In this embodiment, the waveguide 12 is arranged in the exposed state along the manipulator 5. Alternatively, if the waveguide 12 is accommodated within the manipulator 5, the external appearance will advantageously be simplified. If there is no problem with medical treatment for the patient, the number of bending or rotating portions of the manipulator 5 and waveguide 12 may be made greater or less than in the embodiment. The power source for the accelerator may be provided midway along the manipulator. The base portion of the manipulator 5 or the platform 3 may be secured to the floor.

If the x-ray treatment apparatus 1 is arranged near an x-ray CT (Computed Tomography) apparatus and their control systems are configured to cooperate with each other, it is possible to treat the patient P by the x-ray treatment apparatus 1 without moving the patient P, after a treatment part is determined by the x-ray CT apparatus. In addition, the x-ray treatment apparatus 1 can more exactly apply x-rays for radiation treatment.

A radiation applying apparatus according to the present invention can be used as a radiation treatment apparatus or an x-ray diagnosis apparatus in medical fields, and as a radiation source for non-destructive inspections in industrial fields.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiation applying apparatus comprising:

a radiation generating device which emits X-ray;

a head unit carrying the radiation generating device;

a positioning device which is joined with the head unit at a distal end portion thereof and positions the head unit such that the X-ray is applied to an object for radiation application;

a Klystron which is disposed on a proximal end side of the positioning device apart from the head unit and supplied the radiation generating device with power for generating the X-ray;

a waveguide provided along the positioning device between the Klystron and the radiation generating device, and a plurality of rotary RF couplers are provided at several positions in the waveguide.

2. A radiation applying apparatus according claim 1, wherein the positioning device comprising a base portion, a first arm, a second arm and a head mount;

the head unit is mounted on the head mount;

the waveguide is provided with rotary RF couplers at positions corresponding to bent portions between the base portions and the first arm, between the first arm and the second arm, between the second arm and the mount, and between the head mount and the head unit, respectively.

3. A radiation applying apparatus comprising:

an electron gun which emits electrons;

a target which emits x-rays upon being hit by the electrons;

an accelerator arranged between the electron gun and the target and accelerates the electrons;

a head unit accommodating the electron gun and the target and the accelerator;

a positioning device which is a cantilever-type manipulator joined with the head unit at a distal end portion thereof and positions the head unit with a multi-axis control relative to an object for radiation application such that the x-rays are applied to the object;

a Klystron which is disposed on a proximal end side of the positioning device apart from the head unit and supplies the accelerator with power, and a waveguide provided along the positioning device between the Klystron and the accelerator.

4. A radiation applying apparatus comprising:

a head unit accommodating a radiation generating device which accelerates electrons emitted from an electron gun through an accelerator and lets the electrons strike a target to produce X-ray;

a manipulator having the head unit at a distal end portion thereof and operating under a multi-axis control;

an accelerator power source which is disposed on a proximal end side of the manipulator apart from the head unit and supplied power to the accelerator; and a waveguide provided along the manipulator between the accelerator power source and the accelerator.

5. A radiation applying apparatus comprising:

a head unit accommodating an x-ray generating device which accelerates electrons emitted from an electron gun with microwaves and lets the electrons strike a target to produce x-rays;

a manipulator having the head unit at a distal end portion thereof and operating under a multi-axis control;

a microwave source provided on a proximal end side of the manipulator and apart from the head unit; and a waveguide which is provided along the manipulator and supplies microwaves from the microwave source to the x-ray generating device.

6. A radiation applying apparatus according to claim 5, wherein the microwave source is a Klystron.

7. A radiation applying apparatus according to claim 5, wherein the manipulator is provided movable along rails.

8. A radiation applying apparatus according to claim 5, wherein the manipulator has a cantilever-type structure comprising a plurality of rotatable connecting portions and mounting the head unit at a distal end portion thereof.

9. A radiation applying apparatus according to claim 5, wherein the radiation applying apparatus is applicable to medical uses.

* * * * *